United States Patent [19]

Schultze

[11] Patent Number: 4,761,472

[45] Date of Patent: Aug. 2, 1988

[54] ISOLATION AND PURIFICATION OF HEMIN

[75] Inventor: Hans Schultze, Moorrege, Fed. Rep. of Germany

[73] Assignee: BASF Aktiengesellschaft, Fed. Rep. of Germany

[21] Appl. No.: 22,819

[22] Filed: Mar. 6, 1987

[30] Foreign Application Priority Data

Mar. 12, 1986 [DE] Fed. Rep. of Germany ....... 3608091

[51] Int. Cl.$^4$ ........................................... C07D 487/22
[52] U.S. Cl. .................................................. 540/145
[58] Field of Search ........................................ 540/145

[56] References Cited

U.S. PATENT DOCUMENTS 4,330,463  5/1982  Luijerink ......................... 260/112 B

FOREIGN PATENT DOCUMENTS 1055489  5/1979  Canada .
0068537  1/1983  European Pat. Off. .
2526596  1/1976  Fed. Rep. of Germany .

OTHER PUBLICATIONS

Ullmanns Encyklopadie der Technischen Chemie, IVth Ed., vol. 2, 1976, pp. 129–130.
Hoppe-Seyler's Zeitschrift fur Physiologische Chemie, vol. 80, 1912, pp. 35–44.

Primary Examiner—Richard L. Raymond
Attorney, Agent, or Firm—Keil & Weinkauf

[57] ABSTRACT

Hemin is isolated from acidic aqueous solution, and is purified, by crystallization in the presence of a cationic, nonionic or amphoteric surfactant as a crystallization catalyst.

4 Claims, No Drawings

ISOLATION AND PURIFICATION OF HEMIN

The present invention relates to a process for isolating and purifying hemin by catalysed crystallization from aqueous solution or suspension. It is usually impossible to crystallize hemin from aqueous solution.

In the conventional processes, hemin can be isolated from blood or hemoglobin only with the use of disproportionately large amounts of organic solvents. In industrial production, these solvents constitute by far the greatest cost factor and furthermore give rise to environmental problems.

As early as 1853, Teichmann obtained crystals of hemin, which were named after him, by the action of glacial acetic acid on blood in the presence of sodium chloride. This microscopic blood detection method was subsequently developed into a procedure by Schalfejew and is still described today as the conventional method for the preparation of hemin (Ullmann, Encyklopädie d. tech. Chemie, IV edition, 1976, Vol. 11, page 129). In this process, about 800 l of glacial acetic acid are required for the preparation of 1 kg of hemin, and in addition 5 l of pyridine, 11 l of chloroform and a further 70 l of glacial acetic acid are required for the recrystallization. The yield of pure hemin is only about 70% of theory. About 20% are lost during the recrystallization alone.

Other known processes use methanol (EP-B-No. 68537), ethanol, if necessary as a mixture with glycol or glycerol (DE-A No. 2 526 596), dimethylformamide, methyl ethyl ketone or acetone or (Ztschr. f. physiol. Chem. 80 (1912), 35) for the separation of hemin and globin in acidified hemoglobin. From 200 to 500 l of the stated organic solvents are required for 1 kg of hemin, and a highly contaminated hemin is then obtained.

According to U.S. Pat. No. 4,330,463, hydrochloric acid is added to hemoglobin, the mixture is spray dried and the resulting acidic dry blood is extracted several times with an ethanol/methanol mixture, the hemin going into solution. In this procedure more than 1000 l of solvent are required per kg of hemin.

It is an object of the present invention to provide a process for the isolation and purification of hemin which can be carried out without the use of organic solvents and which gives very pure hemin in very high yield.

We have found that this object is achieved by the process according to the claims. In this process, the hemin is crystallized from aqueous chloride-containing solution or suspension at pH 0.5–2.5 with the aid of a catalyst in the form of a cationic, nonionic or amphoteric surfactant or a mixture of such surfactants.

In general, hemin is obtained from hemoglobin, and the latter is obtained from blood. The equilibrium of the cleavage of hemoglobin into hemin and globin in acidic solution is shifted towards the hemin by the addition of the catalyst, because the hemin then crystallizes out (and is therefore prevented from participating in the reverse reaction). Hence, the process involved is essentially the crystallization and isolation of hemin from mixtures of hemoglobin with globin.

If a dilute hemoglobin solution containing hydrochloric acid is heated, a thick precipitate soon separates out, this precipitate consisting of a mixture of denatured globin, i.e. globin which has become insoluble and hemoglobin. We have found that, if a suitable surfactant is added as a catalyst during this treatment, the hemoglobin is not precipitated, but, surprisingly, Teichmann's hemin crystals are formed in virtually quantitative yield. They settle out on standing. The colorless supernatant liquid consists of a pure globin solution containing hydrochloric acid. Although it is preferable to dilute the hemoglobin solution to 2–8, in particular about 5, % solids content prior to hydrolysis, this is not absolutely essential. The hydrolysis and hemin crystallization also take place in concentrated solution, for example at a solids content of 15%, but the reaction rates are higher i.e. the hemin separates out in such a short time that the crystals remain small and settle out only very slowly, if at all. On the other hand, it is less economical to employ very dilute solutions.

Suitable catalysts are the stated surfactants i.e. surface-acting compounds possessing hydrophilic and hydrophobic groups), while anionic surfactants react in a different way. In principle, any of the large number of commercially available types can be used, those having a fairly high molecular weight being preferred in the case of the nonionic surfactants. To facilitate separation of surfactant and globin (which is most easily precipitated from the mother liquor by neutralization after isolation of the hemin crystals), it is advisable to use surfactants which remain in solution even at neutral pH.

Examples of suitable cation surfactants are quarternary ammonium salts which carry one or two long-chain alkyl radicals in the molecule. Examples of particularly important typical compounds are dimethyl-$C_8$–$C_{18}$-alkylbenzylammonium chlorides, such as benzyldodecyldimethylammonium chloride, and stearyltrimethylammonium chloride, benzyltrimethylammonium chloride, benzylmyristyldimethylammonium chloride, cetylpyridinium chloride and dihydroxyethylmethyloleylammonium chloride. Other examples are fatty amines possessing hydroxyl of hydroxypolyether groups, such as octadecyldiethanolamine or lauryldipolyglycolamine, as well as adducts of ethyleneimine with the salts of fatty amines, and 2-(fatty alkyl)-imidazolines, 2-(fatty alkyl)-benzimidazoles and monoesters of triethanolamine with fatty acids.

Examples of suitable nonionic surfactants are oxyethylation products of natural and synthetic fatty alcohols of 9 or more carbon atoms. Particularly preferred nonionic surfactants in this case are oxyalcohols possessing from 9 to 50 oxyethyl or oxypropyl groups, especially $C_9$ to $C_{11}$, $C_{12}$ to $C_{15}$ and $C_{16}$ to $C_{20}$ cuts. Alkylphenols are also useful, in particular octyl-, nonyl- or dodecylphenol in the form of their derivatives possessing from 8 to 50 oxyethyl and/or oxypropyl groups. Condensates of fatty acids with alkanolamines in the form of derivatives possessing from 8 to 50 oxyethylgroups are also useful surfactants. Other suitable nonionic surfactants are the known polymerization products of ethylene oxide and propylene oxide having molecular weights of from 500 to 2,500, and block copolymers of ethylene oxide and propylene oxide having molecular weights of from 500 to 8,500.

Suitable amphoteric surfactants are a very wide variety of betaines, provided that they carry a long-chain hydrophobic radical, e.g. myristyl betaine or the compounds of the sulfotaurine group.

The various surfactants and surfactant types can also be applied as a mixture. The surfactant concentrations which may be used vary within a wide range and are from 0.005 to 20, preferably from 0.01 to 5, % by weight, based on the solution or suspension employed, 0.025% being the most commonly used concentration.

The chloride ion concentration must at least be sufficient to form the hemin, and is advantageously (substantially) higher than this. It has no well defined upper limit.

If the reaction mixture is heated longer than the time required for crystallization of the hemin, denatured globin separates out, even in the presence of the surfactants. This process is undesirable because a mixture of insoluble hemin with globin is formed in this case. For larger batches, where a longer time is required for heating and cooling the batch, the continuous procedure is therefore preferred so that heating can be carried out for a short time. For this purpose, the reaction mixture to which the surfactant has been added as a catalyst is pumped through a heat exchanger, where it is rapidly heated, if necessary kept at the reaction temperature reached for a further period by passing it through a vessel of suitable volume, and then introduced into a second heat exchanger for rapid cooling. Any medium, such as hot water, glycerol, oil etc., may be used as the heating medium, but it is preferable to use steam which emerges as a condensate under atmospheric pressure, so that boiling of the aqueous reaction mixture is avoided and a temperature just below its boiling point is nevertheless reached. In large plants, it is of course also possible to use steam under superatmospheric pressure if appropriate temperature control is available. The most advantageous results are obtained at 90°–99° C., whereas globin denaturization competes at temperatures substantially below this. The process can be optimally controlled by means of a pump speed adapted to the reaction rate, as described in Examples 2 and 3.

By adding hemin seed crystals, it is possible not only to ensure a precise reaction rate but also to achieve a substantial (up to 99%) saving of surfactant catalyst. The seed crystal suspension is in principle also capable of initiating hemin crystallization without the surfactant catalyst. For this purpose, the crystallization rate would have to be increased to such an extent that crystallization would be complete before the competing globin denaturization, i.e. an appropriately large seed crystal surface area would be required. For example, it would be possible to use a large amount of hemin seed crystals, i.e. about 10–100 times more than the amount of hemin crystals formed, and to employ particularly finely milled seed crystals having a mean diameter of less than 1 μm, in which case the hemin formed would also be obtained in a correspondingly fine form, so that centrifugal sepration would difficult. Because of this problem, this process (which is not claimed here) is scarcely important in practice, although it has the advantage that no foreign substance capable of contaminating the hemin or the globin is introduced. Although the surfactant catalyst used according to the invention is such a foreign substance, it gives such large hemin crystals that the latter settle out spontaneously, i.e. without centrifuging, and, since the surfactants, in contrast to the globin, remain in solution during the neutralization of the globin hydrochloride solution, they can readily be removed again. The hemin crystals are freed from surfactant residues by washing with water.

The use of a surfactant catalyst is also suitable for recrystallizing crude hemin with minimum loss of substance. Crude hemin is understood as being not only the reaction product obtained in Examples 2 to 4 but also any other hemin-containing residues, as formed, for example, in enzymatic hemoglobin degradation (cf. Example 8), or simply in pure hemin. The surfactant concentration in this case is advantageously chosen to be higher, for example from 0.1 to 20, most commonly 5, % by weight, based on solution. Hemin in solution or precipitated in amorphous form can be crystallized directly, whereas crystalline hemin must first be dissolved in ammonia water. Instead of ammonia, it is also possible to use any other base, although the solutions are frequently more unstable. It is also possible to dissolve the crude hemin in an organic solvent, such as dimethylformamide or dimethyl sulfoxide, and then to add surfactant-containing water until the mixture predominantly contains water as the solvent, and to allow the hemin to crystallize from this mixture.

The crystallization described in Examples 5 to 8, to effect purification, leads to Teichmann crystals of a specific size. Particularly large crystals are obtained when a large amount of surfactant is used and stirring is not carried out during crystal formation (Example 7), or particularly small crystals are produced when a small amount of nonionic surfactant is heated with stirring (Example 6) and rapid addition of hydrochloric acid. Seed crystals are not required here.

If an ammoniacal hemin solution which contains surfactant catalyst is rapidly acidified with hydrochloric acid, a hemin precipitate containing crystal defects, for example curved rows of needles or nodules, is formed. However, if a neutral solution is used, for example a solution in dimethylformamide, normal crystals are formed. We have found that normal crystal forms are also obtained from ammoniacal solution if heating is first effected at a pH of from 2 to 5 before hydrochloric acid is added slowly until the first crystals form.

When HCl is added more rapidly, the crystals become smaller and sharper, which is generally undesirable from the point of view of smooth isolation. The particular surfactant also has a clearly detectable, specific effect on the crystal shape, which may then be thinner or more fibrous or broader to more lobate, may exhibit a more intense cross-over pattern up to a star shape, etc.

Crude hemins contaminated with globin protein are, if necessary, subjected to enzymatic hydrolysis, for example with pepsin, in order to facilitate recrystallization and isolation of the hemin. Since repeated suspension in water followed by settling out frequently gives hemin having a purity of only 90%, a further treatment in 50–70% strength sulfuric acid may also be carried out, as described in Example 5, the purity increasing to above 98%.

EXAMPLE 1

Ox blood was centrifuged, after the addition of trisodium citrate, and the remaining concentrate of blood corpuscles was brought to a solids content of 5% by dilution with water. 20% strength hydrochloric acid was then added until the pH was 1.5.

500 ml of this starting solution was stirred with 10 g of benzyldodecyldimethylammonium chloride and heated to the boil in the course of 10 minutes on a magnetic stirrer. After about 3 minutes, the reddish brown solution became colorless and small blackish violet hemin crystals were precipitated. The mixture was cooled with water and the crystals were allowed to settle out. The virtually colorless supernatant solution of globin in hydrochloric acid could readily be decanted. The sediment of crystalline hemin was filtered off under suction, washed and dried to give 0.76 g (100% of theory) of 96.5% pure product.

EXAMPLE 2

10 l of the starting solution described in Example 1 and having a pH of 1.5 was stirred with 24 g of cocamidopropyl betaine (a 1-$C_7$-$C_{17}$-alkoylamido-3-dimethylammoniopropane-3-carboxymethylbetaine) and 0.2 g of a 4% strength seed crystal suspension obtained by finely milling an aqueous hemin crystal suspension in a stirred bore mill at about 400 rpm for 6 hours (mean particle diameter 1 μm).

The solution was pumped continuously from below through a vertical, jacketed, steam-heated glass tube having a length of 1.40 m and a diameter of 20 mm and then cooled to a maximum temperature of 55° C. using a laboratory condenser. The delivery rate was set so that the emerging reaction solution was no longer brown, this corresponding to a velocity of about 80 ml per minute under the stated conditions. Separation was effected using a small continuous centrifuge (about 3,000×g), and 10 l of a pale yellowish globin hydrochloride solution and 170 g of moist crude hemin containing a little globin were obtained. Further working up was carried out as described in Example 5.

EXAMPLE 3

600 l of the starting solution described in Example 1 were stirred with 150 g of nonylphenol polyglycol ether (degree of polymerization 30) and 20 g of the 4% strength hemin seed crystal suspension of Example 2.

The solution was pumped continuously from below through a vertical steam-heated tubular heat exchanger having a length of 1 m and possessing 46 stainless steel tubes each having a diameter of 12 mm, and was passed via a 6 l tubular section, as a post reactor, and a cooler having a cooling area of about 0.1 $m^2$ into a continuously discharging separator having a 3 l drum and a centrifugal force of about 5,000×g. The delivery rate of the pump was about 250 l per hour and was controlled so that the solution no longer had a brown color on entering the centrifuges. The centrifugate consisted of about 600 l of pale yellow globin hydrochloride solution, while the residue comprised 4.2 kg of moist, globin-containing crude hemin. The crude hemin was worked up as described in Example 5.

EXAMPLE 4

The experiment of Example 3 was repeated with 5 times the amount of the same surfactant (0.75 kg) and with only 1/10 of the amount of seed crystals (2 g of suspension). The reaction rate was the same as in Example 3. 600 l of globin solution containing hydrochloric acid and 4.4 kg of moist crude hemin were obtained.

EXAMPLE 5

The crude hemin obtained in Examples 2 to 4 was rendered stirrable by adding water and was stirred for 2 hours with 1 g of pepsin per 2 l of suspension, at from 30° to 40° C. The mixture was then cooled with ice to +5° C., and the hemin was just brought completely into solution by adding ammonia. Nonylphenol polyglycol ether (degree of polymerization 30) and citric acid were then added, each in an amount equal to the expected yield of hemin, and the mixture was heated for 10 minutes at about 95° C. An amount of hydrochloric acid equivalent to the amount of ammonia used was then added to the stirred mixture, and further hydrochloric acid was added slowly at 95° C. until crystallization of hemin began (microscope). After one to two hours, the amorphous, brownish black lumps had completely disappeared and in their place a corresponding number of Teichmann hemin crystals of very uniform size and with an edge length of about 0.02 mm had formed.

The crystals were allowed to settle out, the solution was decanted and 85% strength sulfuric acid was added to the stirred residue until a concentration of 60% of sulfuric acid was reached. After 10 minutes, the mixture was diluted with twice its volume of water, and the crystals were allowed to settle out and were washed acid-free with water on the suction filter. The yield was quantitative. The purity was 98%, measured as the specific extinction in NaOH at 388 nm (1%, 1 cm), which is 956 for 100% pure hemin.

Fe calculated: 8.57%, found: 8.4%
Cl calculated: 5.44%, found: 5.3%

EXAMPLE 6

The recrystallization in Example 5 was repeated using 1/10 of the amount of catalyst. Substantially smaller hemin crystals were formed.

EXAMPLE 7

The recrystallization described in Example 5 was repeated with the same total amount of a catalyst mixture consisting of equal amounts of the surfactants of Examples 1 and 5, and stirring was not carried out during crystallization. Substantially larger hemin crystals having an edge length of about 0.1 mm were formed.

EXAMPLE 8

40 l of the starting solution described in Example 1 was stirred with 10 g of pepsin for 16 hours at 37° C., after which the mixture was passed through a continuous centrifuge having a drum capacity of 3 l and operated at a centrifugal force of about 5,000×g.

2 kg of hemin-containing residue were obtained, this residue having a solids content of 12%. It was diluted with 2 l of water, 60 g of the catalyst of Example 3 were added and the mixture was heated to 95° C. Crystallization was initiated by first adding 150 ml of 20% strength hydrochloric acid and then adding 10 ml portions of this acid at intervals. The further procedure was as described in Examples 5 to 7.

Yield: 60 g of crystalline hemin
Purity: 98%

I claim:

1. A process for the isolation and purification of hemin, where the hemin is allowed to crystallize out from a heated aqueous hydrogen chloride-containing solution or suspension at pH 0.5–2.5 in the presence of a cationic, nonionic or amphoteric surfactant which remains in solution at neutral pH, or a mixture thereof, as a crystallization catalyst.

2. The process of claim 1, wherein the crystallization of hemin is carried out continuously.

3. The process of claim 1 wherein the catalytic crystallization is supported by the addition of microcrystalline seed crystals.

4. The process of claim 1, wherein a surfactant concentration of from 0.005 to 20% by weight, based on the solution or suspension used, is employed.

* * * * *